United States Patent
Dwork et al.

(10) Patent No.: US 11,717,407 B2
(45) Date of Patent: *Aug. 8, 2023

(54) TRANSCATHETER VALVE PROSTHESIS HAVING AN EXTERNAL SKIRT FOR SEALING AND PREVENTING PARAVALVULAR LEAKAGE

(71) Applicant: Medtronic Vascular, Inc., Santa Rosa, CA (US)

(72) Inventors: Joshua Dwork, Santa Rosa, CA (US); Scott Mosher, San Francisco, CA (US)

(73) Assignee: MEDTRONIC VASCULAR, INC., Santa Rosa, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/255,184

(22) Filed: Jan. 23, 2019

(65) Prior Publication Data
US 2019/0151091 A1  May 23, 2019

Related U.S. Application Data

(62) Division of application No. 14/533,541, filed on Nov. 5, 2014, now Pat. No. 10,213,307.

(51) Int. Cl.
| | |
|---|---|
| *A61F 2/24* | (2006.01) |
| *A61F 2/06* | (2013.01) |
| *A61F 2/90* | (2013.01) |

(52) U.S. Cl.
CPC .......... *A61F 2/2469* (2013.01); *A61F 2/2412* (2013.01); *A61F 2/2418* (2013.01);
(Continued)

(58) Field of Classification Search
CPC .... A61F 2230/0067; A61F 2/24; A61F 2/013; A61F 2/90; A61F 2/915;
(Continued)

(56) References Cited

U.S. PATENT DOCUMENTS

| | | |
|---|---|---|
| 5,571,175 A | 11/1996 | Vanney et al. |
| 7,276,078 B2 | 10/2007 | Spenser et al. |

(Continued)

FOREIGN PATENT DOCUMENTS

| | | |
|---|---|---|
| EP | 0537487 A1 | 4/1993 |
| WO | 2009094501 A1 | 7/2009 |

(Continued)

OTHER PUBLICATIONS

PCT/US2015/056510 "The International Search Report and the Written Opinion" dated Jan. 21, 2016.

(Continued)

*Primary Examiner* — Ann Schillinger
(74) *Attorney, Agent, or Firm* — Medler Ferro Woodhouse & Mills PLLC

(57) ABSTRACT

A transcatheter valve prosthesis including a tubular stent includes an interior skirt or skirt portion is coupled to and covers an inner circumferential surface of the stent, and an exterior skirt or skirt portion is coupled to and covers an outer circumferential surface of the stent. A prosthetic valve component is disposed within and secured to the interior skirt or skirt portion. The interior and exterior skirts or skirt portions may overlap to form a double layer of skirt material on the stent, or may be portions of a skirt that do not overlap such that only a single layer of skirt material covers the stent. When the stent is in at least the compressed configuration, at least one endmost crown may be positioned radially inwards with respect to the remaining endmost crowns formed at the inflow end of the stent in order to accommodate the exterior skirt.

18 Claims, 11 Drawing Sheets

(52) U.S. Cl.
CPC ... *A61F 2210/00* (2013.01); *A61F 2220/0075* (2013.01); *A61F 2230/008* (2013.01)

(58) Field of Classification Search
CPC ...... A61F 2220/0075; A61F 2250/0069; A61F 2/06; A61F 2/2475; A61F 2002/072; A61F 2002/075; A61F 2210/0061
See application file for complete search history.

(56) References Cited

U.S. PATENT DOCUMENTS

| | | |
|---|---|---|
| 7,331,991 B2 | 2/2008 | Kheradvar et al. |
| 7,628,805 B2 | 12/2009 | Spenser et al. |
| 7,708,775 B2 | 5/2010 | Rowe et al. |
| 7,780,725 B2 | 8/2010 | Haug et al. |
| 8,002,825 B2 | 8/2011 | Letac et al. |
| 8,182,528 B2 | 5/2012 | Salahieh et al. |
| 8,231,670 B2 | 7/2012 | Salahieh et al. |
| 8,449,599 B2 | 5/2013 | Chau et al. |
| 8,603,160 B2 | 12/2013 | Salahieh et al. |
| 8,623,078 B2 | 1/2014 | Salahieh et al. |
| 8,628,566 B2 | 1/2014 | Eberhardt et al. |
| 8,641,757 B2 | 2/2014 | Pintor et al. |
| 8,668,733 B2 | 3/2014 | Haug et al. |
| 8,673,000 B2 | 3/2014 | Tabor et al. |
| 8,734,484 B2 | 5/2014 | Ahlberg et al. |
| 8,795,357 B2 | 8/2014 | Yohanan et al. |
| 8,801,706 B2 | 8/2014 | Rothstein et al. |
| 8,802,356 B2 | 8/2014 | Braido et al. |
| 10,213,307 B2 * | 2/2019 | Dwork .................. A61F 2/2418 |
| 2001/0007956 A1 | 7/2001 | Letac et al. |
| 2003/0199963 A1 | 10/2003 | Tower et al. |
| 2003/0199971 A1 | 10/2003 | Tower et al. |
| 2004/0030381 A1 | 2/2004 | Shu |
| 2004/0111111 A1 | 6/2004 | Lin |
| 2004/0122514 A1 | 6/2004 | Fogarty et al. |
| 2005/0137682 A1 | 6/2005 | Justino |
| 2006/0004442 A1 | 1/2006 | Spenser et al. |
| 2007/0270944 A1 | 11/2007 | Bergheim et al. |
| 2007/0293944 A1 | 12/2007 | Spenser et al. |
| 2008/0009940 A1 | 1/2008 | Cribier |
| 2008/0243245 A1 | 10/2008 | Thambar et al. |
| 2009/0099653 A1 | 4/2009 | Suri et al. |
| 2009/0112311 A1 | 4/2009 | Miles et al. |
| 2009/0192591 A1 | 7/2009 | Ryan et al. |
| 2010/0036479 A1 | 2/2010 | Hill et al. |
| 2010/0168844 A1 | 7/2010 | Toomes et al. |
| 2010/0198238 A1 | 8/2010 | Sorajja |
| 2010/0277413 A1 | 11/2010 | Wang et al. |
| 2010/0280589 A1 | 11/2010 | Styrc |
| 2011/0022157 A1 * | 1/2011 | Essinger ............... A61F 2/2418 623/1.11 |
| 2011/0054466 A1 | 3/2011 | Rothstein et al. |
| 2011/0098802 A1 | 4/2011 | Braido et al. |
| 2011/0137397 A1 | 6/2011 | Chau et al. |
| 2011/0172765 A1 | 7/2011 | Nguyen et al. |
| 2011/0245911 A1 | 10/2011 | Quill et al. |
| 2011/0257721 A1 | 10/2011 | Tabor |
| 2011/0264206 A1 | 10/2011 | Tabor |
| 2012/0022633 A1 * | 1/2012 | Olson ................... A61F 2/2433 623/1.11 |
| 2012/0041549 A1 | 2/2012 | Salahieh et al. |
| 2012/0041550 A1 | 2/2012 | Salahieh et al. |
| 2013/0190857 A1 | 7/2013 | Mitra et al. |
| 2013/0190862 A1 | 7/2013 | Pintor et al. |
| 2013/0197622 A1 | 8/2013 | Mitra et al. |
| 2013/0304200 A1 * | 11/2013 | McLean ................ A61F 2/2418 623/2.18 |
| 2013/0331929 A1 | 12/2013 | Mitra et al. |
| 2014/0046426 A1 | 2/2014 | Kovalsky |
| 2014/0114402 A1 | 4/2014 | Ahlberg et al. |
| 2014/0114406 A1 | 4/2014 | Salahieh et al. |
| 2014/0194975 A1 | 7/2014 | Quill et al. |
| 2014/0194981 A1 | 7/2014 | Menk et al. |
| 2014/0222144 A1 | 8/2014 | Eberhardt et al. |
| 2014/0236287 A1 | 8/2014 | Clague et al. |
| 2014/0243966 A1 | 8/2014 | Garde et al. |
| 2014/0243969 A1 | 8/2014 | Venkatasubramanian et al. |
| 2014/0257475 A1 | 9/2014 | Gross et al. |
| 2014/0277388 A1 | 9/2014 | Skemp |
| 2014/0277417 A1 * | 9/2014 | Schraut ................ A61F 2/2403 623/2.17 |
| 2014/0277419 A1 | 9/2014 | Garde et al. |
| 2014/0277423 A1 | 9/2014 | Alkhatib et al. |
| 2014/0277424 A1 | 9/2014 | Oslund |
| 2014/0277425 A1 | 9/2014 | Dakin |
| 2014/0277426 A1 | 9/2014 | Dakin et al. |
| 2014/0277428 A1 | 9/2014 | Skemp et al. |

FOREIGN PATENT DOCUMENTS

| | | |
|---|---|---|
| WO | 2011051043 A1 | 5/2011 |
| WO | 2012032187 A1 | 3/2012 |
| WO | 2013033791 A1 | 3/2013 |
| WO | 2013059747 A1 | 4/2013 |
| WO | 2014072439 A1 | 5/2014 |

OTHER PUBLICATIONS

"Invitation to Pay Additional Fees", International Application No. PCT/US2014/010734, including annex with Partial International Search Report, dated Apr. 9, 2014.
"International Search Report and Written Opinion", International Application No. PCT/2014/014090, dated Apr. 14, 2014.
Communication pursuant to Article 94(3) EPC dated May 31, 2018 in corresponding European Patent Application No. 15 788 307.5.
Examination Report dated Sep. 21, 2017 in corresponding Australian Patent Application No. 2015343583.

* cited by examiner

TRANSCATHETER VALVE PROSTHESIS HAVING AN EXTERNAL SKIRT FOR SEALING AND PREVENTING PARAVALVULAR LEAKAGE

CROSS-REFERENCE TO RELATED APPLICATION

This application is a divisional of U.S. application Ser. No. 14/533,541 filed Nov. 5, 2014, the disclosure of which is incorporated by reference herein in its entirety.

FIELD OF THE INVENTION

The present invention relates in general to transcatheter valve prostheses, and more particularly to a transcatheter valve prosthesis having one or more components for preventing paravalvular leakage.

BACKGROUND OF THE INVENTION

A human heart includes four heart valves that determine the pathway of blood flow through the heart: the mitral valve, the tricuspid valve, the aortic valve, and the pulmonary valve. The mitral and tricuspid valves are atrioventricular valves, which are between the atria and the ventricles, while the aortic and pulmonary valves are semilunar valves, which are in the arteries leaving the heart. Ideally, native leaflets of a heart valve move apart from each other when the valve is in an open position, and meet or "coapt" when the valve is in a closed position. Problems that may develop with valves include stenosis in which a valve does not open properly, and/or insufficiency or regurgitation in which a valve does not close properly. Stenosis and insufficiency may occur concomitantly in the same valve. The effects of valvular dysfunction vary, with regurgitation or backflow typically having relatively severe physiological consequences to the patient.

Recently, flexible prosthetic valves supported by stent structures that can be delivered percutaneously using a catheter-based delivery system have been developed for heart and venous valve replacement. These prosthetic valves may include either self-expanding or balloon-expandable stent structures with valve leaflets attached to the interior of the stent structure. The prosthetic valve can be reduced in diameter, by crimping onto a balloon catheter or by being contained within a sheath component of a delivery catheter, and advanced through the venous or arterial vasculature. Once the prosthetic valve is positioned at the treatment site, for instance within an incompetent native valve, the stent structure may be expanded to hold the prosthetic valve firmly in place. One example of a stented prosthetic valve is disclosed in U.S. Pat. No. 5,957,949 to Leonhardt et al. entitled "Percutaneous Placement Valve Stent", which is incorporated by reference herein in its entirety. Another example of a stented prosthetic valve for a percutaneous pulmonary valve replacement procedure is described in U.S. Patent Application Publication No. 2003/0199971 A1 and U.S. Patent Application Publication No. 2003/0199963 A1, both filed by Tower et al., each of which is incorporated by reference herein in its entirety.

Although transcatheter delivery methods may provide safer and less invasive methods for replacing a defective native heart valve, leakage between the implanted prosthetic valve and the surrounding native tissue may occur if not accommodated for by a particular implant. For instance, leakage may occur due to the fact that deployment of a minimally invasive cardiac valve is intended to occur without actual physical removal of the diseased or injured heart valve. Rather, the replacement stented prosthetic valve is contemplated to be delivered in a compressed condition to the native valve site, where it is expanded to its operational state within the native valve. Calcified or diseased native leaflets are to be pressed to the side walls of the native valve by the radial force of the stent frame of the prosthetic valve. However, it has been shown that calcified leaflets do not allow complete conformance of a stent frame with a native valve and therefore this ill-fit within the native anatomy may be a source of paravalvular leakage (PVL), as significant pressure gradients across the implanted prosthetic valve may cause blood to leak through the gaps between the implanted prosthetic valve and the calcified anatomy.

Embodiments hereof are related to transcatheter valve prostheses having one or more components attached thereto or integrated thereon to address and prevent paravalvular leakage.

BRIEF SUMMARY OF THE INVENTION

Embodiments hereof relate to a transcatheter valve prosthesis including a tubular stent having a compressed configuration for delivery within a vasculature and an expanded configuration for deployment within a native heart valve. The tubular stent includes a plurality of crowns and a plurality of struts with each crown being formed between a pair of opposing struts, the tubular stent having endmost crowns formed at an inflow end thereof. A skirt is coupled to the tubular stent, with a first portion of the skirt being attached to and covering an inner circumferential surface of the tubular stent and a second portion of the skirt being attached to and covering an outer circumferential surface of an inflow end of the tubular stent. The skirt is continuous from the first portion to the second portion such that the first and second portions do not overlap. A prosthetic valve component is disposed within and secured to the first portion of the skirt. When the tubular stent is in at least the compressed configuration at least one endmost crown is positioned radially inwards with respect to the remaining endmost crowns formed at the inflow end of the tubular stent.

According to another embodiment hereof, a transcatheter valve prosthesis includes a tubular stent having a compressed configuration for delivery within a vasculature and an expanded configuration for deployment within a native heart valve. The tubular stent includes a plurality of crowns and a plurality of struts with each crown being formed between a pair of opposing struts. The plurality of crowns and the plurality of struts define a plurality of openings of the tubular stent and the tubular stent has endmost crowns and endmost openings formed at an inflow end thereof. An interior skirt is coupled to and covers an inner circumferential surface of the tubular stent. A prosthetic valve component is disposed within and secured to the interior skirt. An exterior skirt is coupled to and covers an outer circumferential surface of the tubular stent. The exterior skirt longitudinally extends over at least the endmost openings of the tubular stent. When the tubular stent is in at least the compressed configuration at least one endmost crown is positioned radially inwards with respect to the remaining endmost crowns formed at the inflow end of the tubular stent, thereby forming a circumferentially-extending gap between the endmost crowns adjacent to the at least one endmost crown positioned radially inwards in order to provide a low profile while accommodating the exterior skirt.

According to another embodiment hereof, a transcatheter valve prosthesis includes a tubular stent having a compressed configuration for delivery within a vasculature and an expanded configuration for deployment within a native heart valve. A skirt is coupled to the tubular stent, with a first portion of the skirt being attached to and covering an inner circumferential surface of the tubular stent and a second portion of the skirt being attached to and covering an outer circumferential surface of an inflow end of the tubular stent. The skirt is continuous from, the first portion to the second portion such that the first and second portions do not overlap. A prosthetic valve component is disposed within and secured to the first portion of the skirt.

BRIEF DESCRIPTION OF DRAWINGS

The foregoing and other features and advantages of the invention will be apparent from the following description of embodiments hereof as illustrated in the accompanying drawings. The accompanying drawings, which are incorporated herein and form a part of the specification, further serve to explain the principles of the invention and to enable a person skilled in the pertinent art to make and use the invention. The drawings are not to scale.

DETAILED DESCRIPTION OF THE INVENTION

Specific embodiments of the present invention are now described with reference to the figures, wherein like reference numbers indicate identical or functionally similar elements. If utilized herein, the terms "distal" or "distally" refer to a position or in a direction away from the heart and the terms "proximal" and "proximally" refer to a position near or in a direction toward the heart. The following detailed description is merely exemplary in nature and is not intended to limit the invention or the application and uses of the invention. Although the description of the invention is in the context of treatment of heart valves, the invention may also be used where it is deemed useful in other valved intraluminal sites that are not in the heart. For example, the present invention may be applied to venous valves as well. Furthermore, there is no intention to be bound by any expressed or implied theory presented in the preceding technical field, background, brief summary or the following detailed description.

Figure 1:
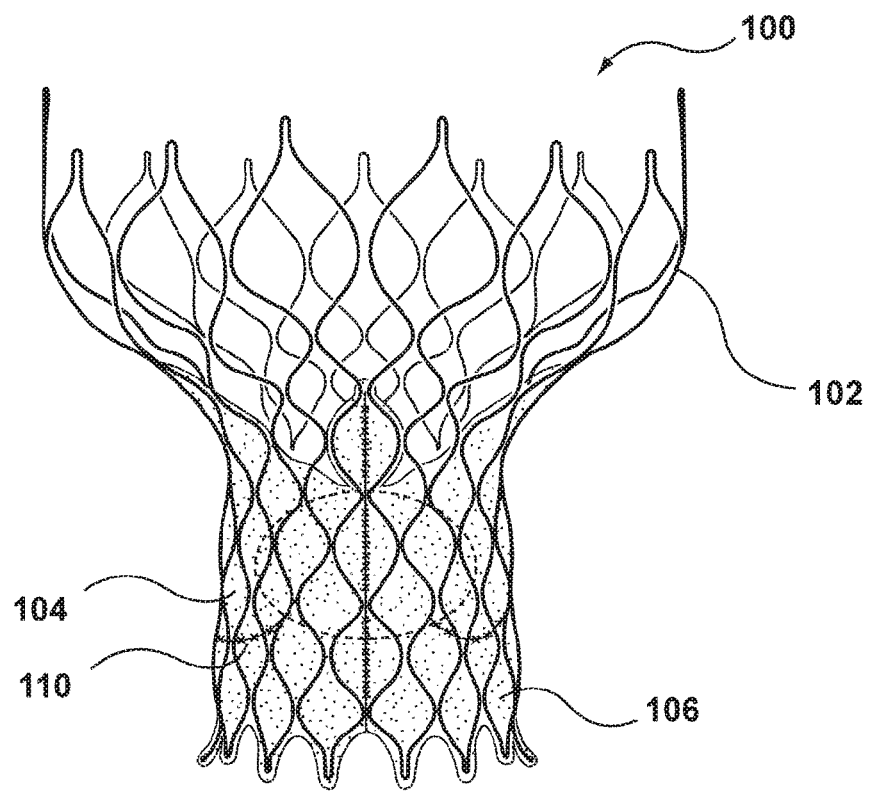
FIG. 1 is a side view illustration of an exemplary or known transcatheter valve prosthesis for use in embodiments hereof.

FIG. 1 depicts an exemplary transcatheter valve prosthesis 100. Transcatheter valve prosthesis 100 is illustrated herein in order to facilitate description of components attached thereto and/or integrated thereon for preventing and/or repairing paravalvular leakage according to embodiments hereof. It is understood that any number of alternate heart valve prostheses can be used with the components for preventing and/or repairing paravalvular leakage described herein. Transcatheter valve prosthesis 100 is merely exemplary and is described in more detail in U.S. Patent Application Pub. No. 2011/0172765 to Nguyen et al., which is incorporated by reference herein in its entirety.

Figure 2:
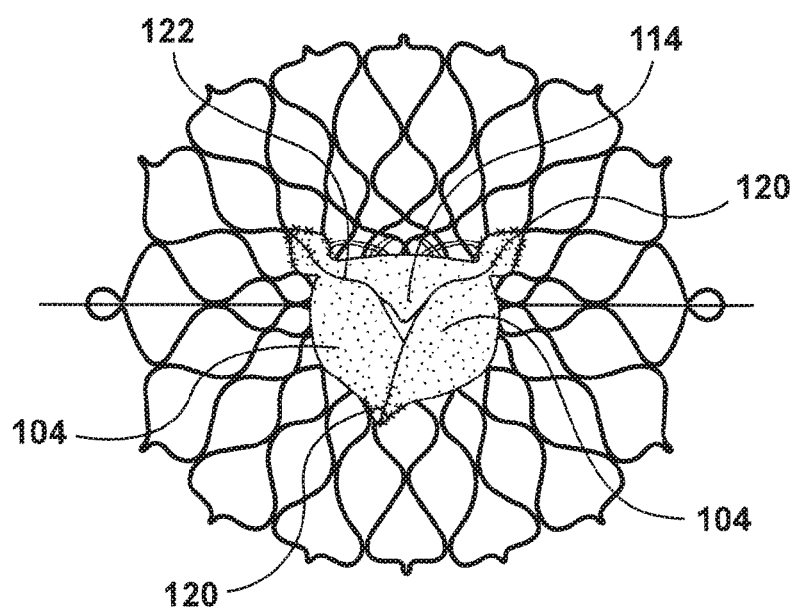
FIG. 2 is a top view illustration of the transcatheter valve prosthesis of FIG. 1.

Transcatheter valve prosthesis 100 includes an expandable stent or frame 102 that supports a prosthetic valve component including one or more valve leaflets 104 within the interior of stent 102. The prosthetic valve component is capable of blocking flow in one direction to regulate flow there-through via valve leaflets 104 that may form a bicuspid or tricuspid replacement valve. Valve leaflets 104 are attached to an interior skirt or graft material 106 which encloses or lines a portion of stent 102 as would be known to one of ordinary skill in the art of prosthetic tissue valve construction. Valve leaflets 104 are sutured or otherwise securely and sealingly attached along their bases 110 to the interior surface of interior skirt 106. Adjoining pairs of leaflets are attached to one another at their lateral ends to form commissures 120, with free edges 122 of the leaflets forming coaptation edges that meet in area of coaptation 114. FIG. 2 is an end view of FIG. 1 and illustrates an exemplary tricuspid valve having three leaflets 104, although a bicuspid leaflet configuration may alternatively be used in embodiments hereof. More particularly, if transcatheter valve prosthesis 100 is configured for placement within a native valve having three leaflets such as the aortic, tricuspid, or pulmonary valves, transcatheter valve prosthesis 100 includes three valve leaflets 104. If transcatheter valve prosthesis 100 is configured for placement within a native valve having two leaflets such as the mitral valve, transcatheter valve prosthesis 100 includes two valve leaflets 104.

Leaflets 104 may be made of pericardial material; however, the leaflets may instead be made of another material. Natural tissue for replacement valve leaflets may be obtained from, for example, heart valves, aortic roots, aortic walls, aortic leaflets, pericardial tissue, such as pericardial patches, bypass grafts, blood vessels, intestinal submucosal tissue, umbilical tissue and the like from humans or animals. Synthetic materials suitable for use as leaflets 104 include DACRON® polyester commercially available from Invista North America S.A.R.L. of Wilmington, Del., other cloth materials, nylon blends, polymeric materials, and vacuum deposition nitinol fabricated materials. One polymeric material from which the leaflets can be made is an ultra-high molecular weight polyethylene material commercially available under the trade designation DYNEEMA from Royal DSM of the Netherlands. With certain leaflet materials, it may be desirable to coat one or both sides of the leaflet with a material that will prevent or minimize overgrowth. It is further desirable that the leaflet material is durable and not subject to stretching, deforming, or fatigue.

Delivery of transcatheter valve prosthesis 100 may be accomplished via a percutaneous transfemoral approach or a transapical approach directly through the apex of the heart via a thoracotomy, or may be positioned within the desired area of the heart via different delivery methods known in the art for accessing heart valves. During delivery, if self-expanding, the prosthetic valve remains compressed until it reaches a target diseased native heart valve, at which time transcatheter valve prosthesis 100 can be released from the delivery catheter and permitted to expand in situ via self-expansion. The delivery catheter is then removed and transcatheter valve prosthesis 100 remains deployed within the native target heart valve. Alternatively, transcatheter valve prosthesis 100 may be balloon-expandable and delivery thereof may be accomplished via a balloon catheter as would be understood by one of ordinary skill in the art.

Figure 3:
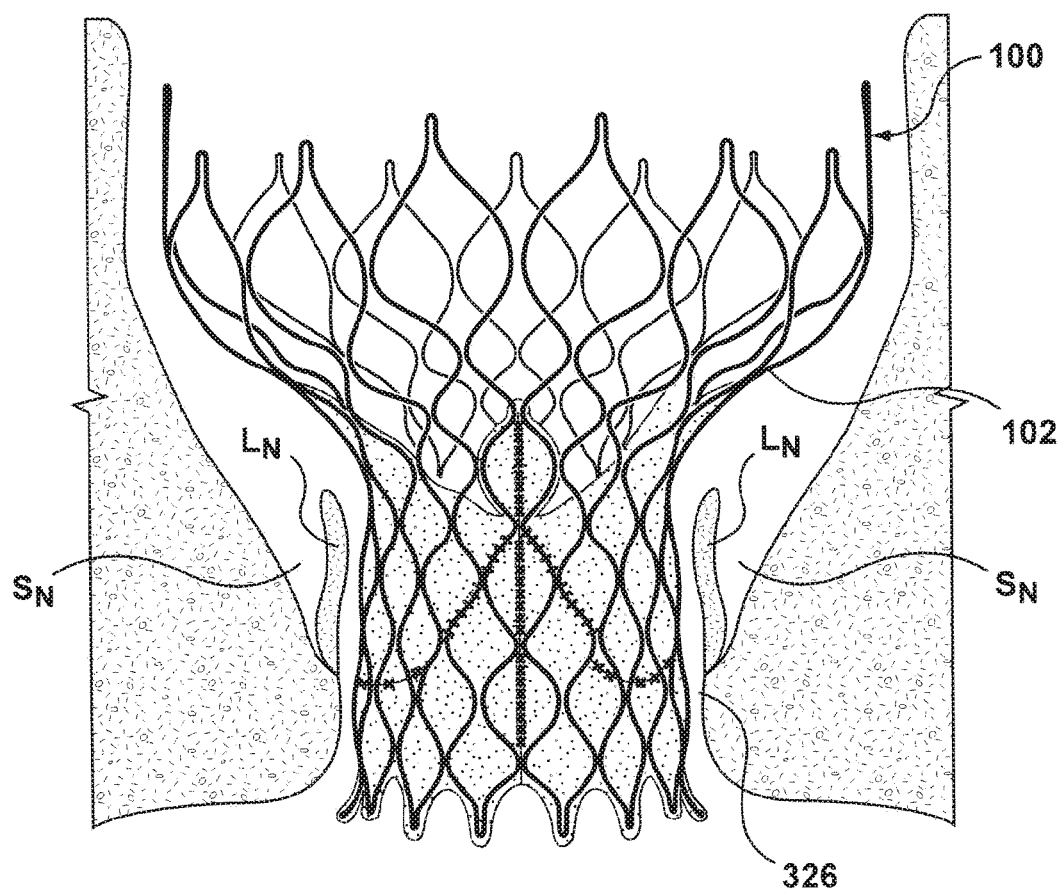
FIG. 3 is a side view illustration of the transcatheter valve prosthesis of FIG. 1 implanted within a native valve annulus.

FIG. 3 is a side view illustration of transcatheter valve prosthesis 100 implanted within a native aortic heart valve, which is shown in section, having native leaflets $L_N$ and corresponding native sinuses $S_N$. When transcatheter valve prosthesis 100 is deployed within the valve annulus of a native heart valve, stent 102 is configured to be expanded within native valve leaflets $L_N$ of the patient's defective valve, to thereby retain the native valve leaflets in a permanently open state. The native valve annulus may include surface irregularities on the inner surface thereof, and as a result one or more gaps or cavities/crevices 326 may be present or may form between the perimeter of transcatheter valve prosthesis 100 and the native valve annulus. For example, calcium deposits may be present on the native valve leaflets (e.g., stenotic valve leaflets) and/or shape differences may be present between the native heart valve annulus and prosthesis 100. More particularly, in some cases native annuli are not perfectly rounded and have indentations corresponding to the commissural points of the native valve leaflets. As a result, a prosthesis having an approximately circular cross-section does not provide an exact fit in a native valve. These surface irregularities, whatever their underlying cause, can make it difficult for conventional prosthetic valves to form a blood tight seal between the prosthetic valve and the inner surface of the valve annulus, causing undesirable paravalvular leakage and/or regurgitation at the implantation site.

Embodiments hereof relate to a transcatheter valve prosthesis having an exterior skirt that encircles or surrounds an outer surface of the transcatheter valve prosthesis in order to occlude or fill gaps between the perimeter of a transcatheter valve prosthesis and the native valve annulus, thereby reducing, minimizing, or eliminating leaks there-between. More particularly, with reference to FIG. 4, a side view of a transcatheter valve prosthesis 400 is shown in its expanded or deployed configuration. Similar to transcatheter valve prosthesis 100, transcatheter valve prosthesis 400 includes a tubular stent 402, an interior skirt 406 coupled to and covering an inner circumferential surface of stent 402, and a prosthetic valve component that includes leaflets 404 disposed within and secured to interior skirt 406. However, unlike transcatheter valve prosthesis 100, transcatheter valve prosthesis 400 also includes exterior skirt 434 coupled to and covering an outer circumferential surface of stent 402 for sealing and preventing paravalvular leakage. Exterior skirt 434 functions to block any retrograde flow within the native valve, thereby preventing undesired regurgitation and preventing blood stagnation in and around the native valve sinuses. In addition, when transcatheter valve prosthesis 400 is deployed, exterior skirt 434 fills any/all gaps or cavities/crevices between the outer surface of stent 402 and native valve tissue such that blood flow through the target gap or cavity is occluded or blocked, or stated another way blood is not permitted to flow there-through. Exterior skirt 434 functions as a continuous circumferential seal around transcatheter valve prosthesis 400 to block or prevent blood flow around the outer perimeter of the prosthesis, thereby minimizing and/or eliminating any paravalvular leakage at the implantation site.

Conventionally when additional exterior skirt material is added to a transcatheter valve prosthesis, some portions of a self-expanding stent may be inadvertently pushed or displaced radially inward when the transcatheter valve prosthesis is compressed or contracted into a sheath for delivery. More particularly, when a transcatheter valve prosthesis without an exterior skirt, such as transcatheter valve prosthesis 100 described above, is compressed or contracted into a, sheath of a delivery catheter, the struts of stent 102 are compressed to abut against each together in order to fit into the sheath and the outer surface of each strut presses against the inner surface of the sheath. The material of interior skirt 106 compresses or packs into the lumen of stent 102. However, when an exterior skirt is added to a transcatheter valve prosthesis, the extra material may cause a portion of the stent to be pushed inwardly and any portions of the stent that are pushed inwardly no longer press against the inner surface of the sheath of the delivery catheter. With the addition of an exterior skirt and no further modifications to either the valve prosthesis or the delivery system, such as using a delivery system with a wider lumen diameter and also a greater delivery profile, the delivery configuration is unpredictable and may lead to erratic loading forces, deployment forces, and/or recapture forces. In order to accommodate the addition of exterior skirt 434, stent 402 is formed such that at least one endmost crown thereof is positioned radially inwards with respect to the remaining endmost crowns as will be described in more detail herein.

Figure 4:
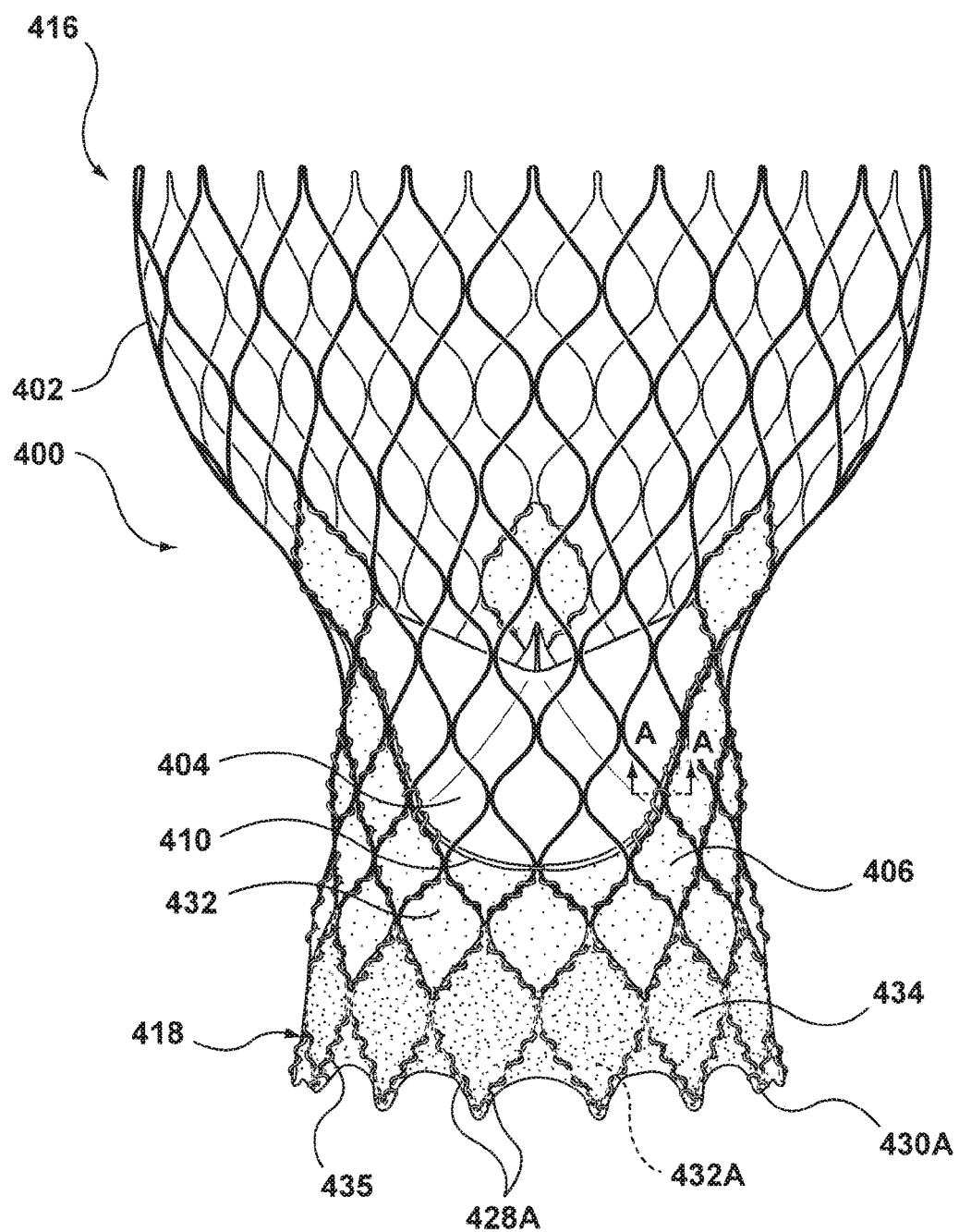
FIG. 4 is a side view illustration of a transcatheter valve prosthesis including a first or interior skirt around an inner surface thereof and a second or exterior skirt around an outer surface thereof, the transcatheter valve prosthesis being shown in a deployed or expanded configuration, wherein at least one endmost crown of the transcatheter valve prosthesis is positioned radially inward in order to accommodate the exterior skirt when the transcatheter valve prosthesis is in a compressed or delivery configuration and wherein the interior skirt and exterior skirt are formed from the same material.

Stent 402 will now be described in more detail. Stent 402 of valve prosthesis 400 has a deployed configuration including an enlarged or flared first end 416 and a second end 418. In the embodiment depicted in FIG. 4, valve prosthesis 400 is configured for replacement for an aortic valve such that second end 418 functions as an inflow or distal end of transcatheter valve prosthesis 400 and extends into and anchors within the aortic annulus of a patient's left ventricle, while first end 416 functions as an outflow or proximal end of transcatheter valve prosthesis 400 and is positioned in the patient's ascending aorta. As alternatives to the deployed configuration of FIG. 4, the stent/valve support frame may have an hourglass configuration or profile 402B shown in FIG. 4B, a generally tubular configuration or profile 402C as shown in FIG. 4C, or other stent configuration or shape known in the art for valve replacement.

Stent 402 is a unitary tubular component having a plurality of side openings 432, which may be formed by a laser-cut manufacturing method and/or another conventional stent forming method as would be understood by one of ordinary skill in the art. In an embodiment, side openings 432 may be diamond-shaped or of another shape. Stent 402 includes a plurality of crowns 430 and a plurality of struts 428 with each crown being formed between a pair of opposing struts. Each crown 430 is a curved segment or bend extending between opposing struts 428. The plurality of crowns 430 and the plurality of struts 428 define the plurality of side openings 432 of the tubular stent 402. More particularly, as best shown in FIG. 4D which is a side view of a single side opening 432 of stent 402, each side opening 432 is formed by, two pairs of opposing crowns 430 and four struts 428 therebetween. Stent 402 has endmost side openings 432A including endmost crowns 430A at inflow or distal end 418 thereof. For sake of clarity, the two struts immediately adjacent to each endmost crown 430A are herein referred to as endmost struts 428A. It will be understood by one of ordinary skill in the art that the illustrated configurations of stent 402 are exemplary and stent 402 may have alternative patterns or configurations. For example, in another embodiment (not shown), stent 402 may include a series of independent or separate sinusoidal patterned rings coupled to each other to form a tubular component.

Figure 4A:
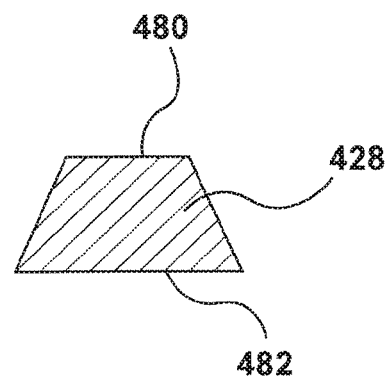
FIG. 4A is a cross-sectional view of a strut of the transcatheter valve prosthesis of FIG. 4 taken along line A-A of FIG. 4.
Figure 4B:
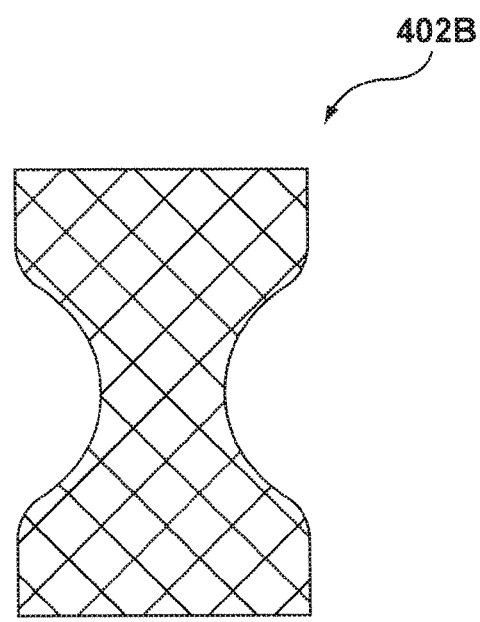
FIG. 4B is a side view illustration of an alternative configuration of a stent profile for use in embodiments hereof.
Figure 4C:
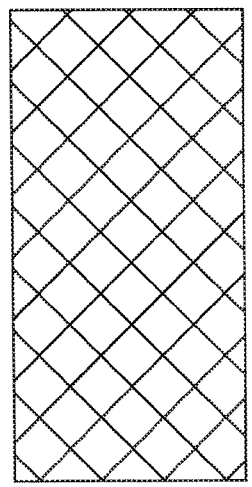
FIG. 4C is a side view illustration of an alternative configuration of a stent profile for use in embodiments hereof.
Figure 4D:
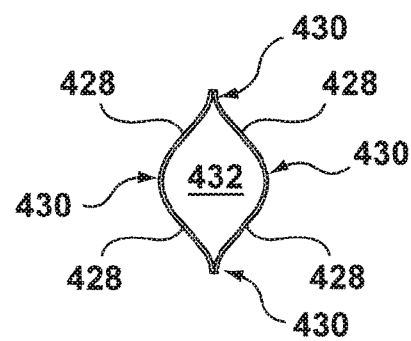
FIG. 4D is a side view of a single side opening of the stent of the transcatheter valve prosthesis of FIG. 4.

With reference to FIG. 4A, in an embodiment hereof, stent 402 is laser cut from a cylindrical tube and the cross-sectional shape of struts 428 and crowns 430, including endmost struts 428A and endmost crowns 430A, are trapezoidal with a shorter face or surface 480 of the trapezoid forming the inner surface of the strut/crown and a longer face or surface 482 of the trapezoid forming the outer surface of the strut/crown. When stent 402 is compressed for delivery, adjacent struts and crowns abut or are pressed together and the mating surfaces thereof aid to prevent any struts or crowns being inadvertently pushed forward.

In embodiments hereof, stent 402 is self-expanding to return to an expanded deployed state from a compressed or constricted delivery state and may be made from stainless steel, a pseudo-elastic metal such as a nickel titanium alloy or Nitinol, or a so-called super alloy, which may have a base metal of nickel, cobalt, chromium, or other metal. "Self-expanding" as used herein means that a structure/component has a mechanical memory to return to the expanded or deployed configuration. Mechanical memory may be imparted to the wire or tubular structure that forms stent 402 by thermal treatment to achieve a spring temper in stainless steel, for example, or to set a shape memory in a susceptible metal alloy, such as nitinol, or a polymer, such as any of the polymers disclosed in U.S. Pat. Appl. Pub. No. 2004/0111111 to Lin, which is incorporated by reference herein in its entirety. Alternatively, transcatheter valve. prosthesis 400 may be made balloon-expandable as would be understood by one of ordinary skill in the art.

Exterior skirt 434 is coupled to the outer surface of transcatheter valve prosthesis 400 around inflow or distal end 418 thereof. Exterior skirt 434 may be attached to stent 402 by any suitable means known to those skilled in the art, for example and not by way of limitation, suture/stitches, welding, adhesive, or mechanical coupling. In an embodiment, stitches 435 surround or extend around the perimeter of each endmost side opening 432A in order to fully secure and fix exterior skirt 434 to the outer surface of transcatheter valve prosthesis 400. When deployed, exterior skirt 434 may be positioned in situ at the native valve annulus, slightly above the valve annulus, slightly below the valve annulus, or some combination thereof. Since the exterior skirt is coupled to the outer surface of transcatheter valve prosthesis 400, longitudinal placement and/or the size and shape thereof may be adjusted or adapted according to each application and to a patient's unique needs. For example, depending on the anatomy of the particular patient, the exterior skirt may be positioned on transcatheter valve prosthesis 400 so that in situ the exterior skirt is positioned between transcatheter valve prosthesis 400 and the interior surfaces of the native valve leaflets, between transcatheter valve prosthesis 400 and the interior surfaces of the native valve annulus, and/or between transcatheter valve prosthesis 400 and the interior surfaces of the left ventricular outflow track (LVOT).

Exterior skirt 434 longitudinally extends over at least endmost side openings 432A of stent 402 but the length of exterior skirt 434 may vary according to application. In an embodiment hereof, as shown in FIG. 4, exterior skirt 434 longitudinally extends over only endmost side openings 432A of stent 402. However, exterior skirt 434 may extend over a longer portion of transcatheter valve prosthesis 400. In another embodiment hereof (not shown), exterior skirt 434 may extend up to bases 410 of leaflets 406. In another embodiment hereof (not shown), exterior skirt 434 may extend to an intermediate position between bases 410 of leaflets 406 and endmost side openings 432A.

Interior skirt 406 is coupled to the inner surface of transcatheter valve prosthesis 400. In the embodiment of FIG. 4, interior skirt 406 longitudinally extends from bases 410 of leaflets 406 to inflow or distal end 418 of transcatheter valve prosthesis 400. As such, in the embodiment of FIG. 4, double layers of skirt material, i.e., a first layer via exterior skirt 434 and a second layer via interior skirt 406, extend over endmost side openings 432A of stent 402. The layers of skirt material, i.e., a first layer via exterior skirt 434 and a second layer via interior skirt 406, overlap or overlay each other around inflow end 418 of valve prosthesis 400. Inflow end 418 is thus sandwiched or positioned between layers of skirt material. However, the length of interior skirt 406 may vary according to application and interior skirt 406 may extend over a shorter portion of transcatheter valve prosthesis 400. In another embodiment hereof (not shown), interior skirt 406 may longitudinally extend from bases 410 of leaflets 406 to a proximal end or edge of exterior skirt 434 such that the layers of skirt material do not overlap or overlay each other.

Although exterior and interior skirts 434, 406 are described herein as separate or individual components with exterior skirt 434 being coupled to an outer surface of stent 402 and interior skirt 406 being coupled to an inner surface of stent 402, in another embodiment hereof (not shown) the skirts may be formed from the same or single component. For example, exterior and interior skirts 434, 406 may be formed via a single folded component that is coupled to both the inner and outer surfaces of stent 402 with the fold thereof extending over or around inflow or distal end 418 of valve prosthesis 400.

Figure 5:
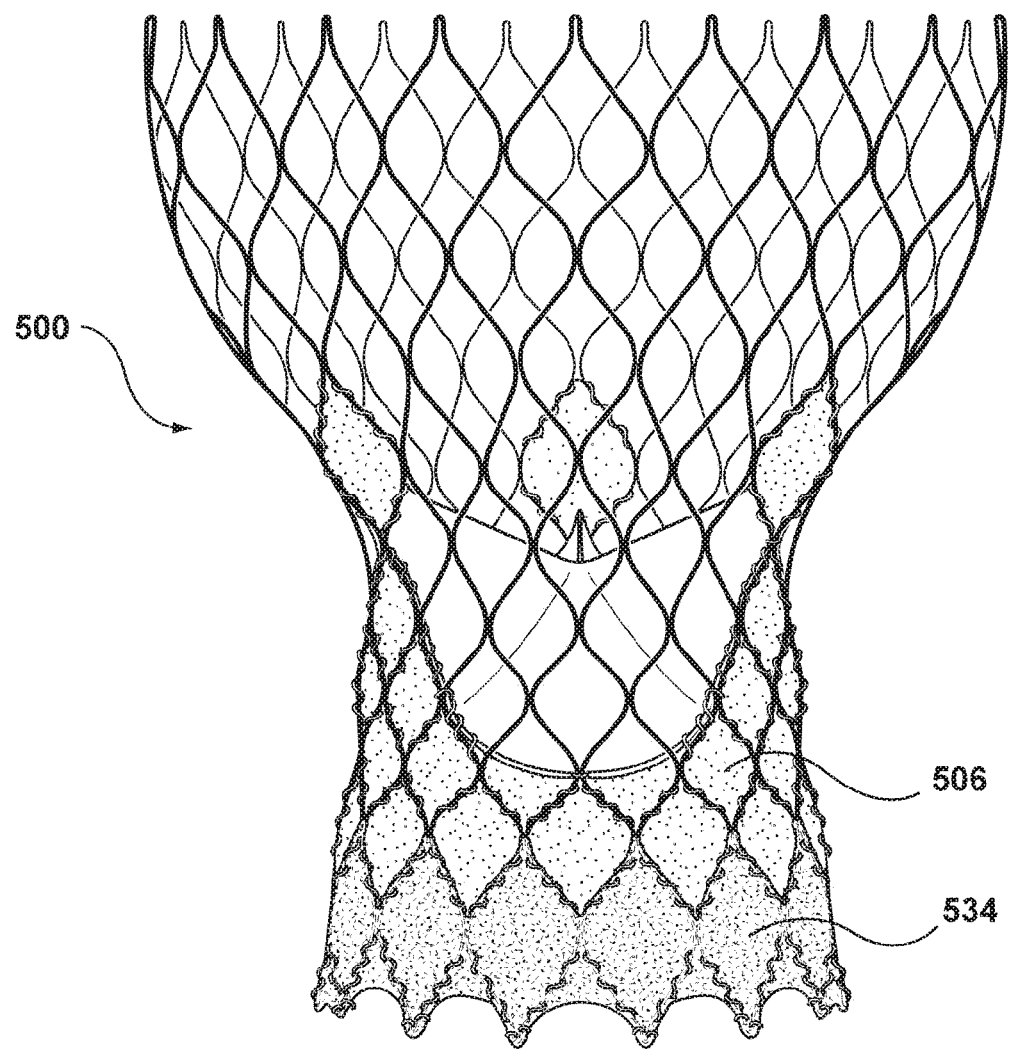
FIG. 5 is a side view illustration of a transcatheter valve prosthesis including an interior skirt around an inner surface thereof and an exterior skirt around an outer surface thereof according to another embodiment hereof, the transcatheter valve prosthesis being shown in a deployed or expanded configuration, wherein the interior skirt and exterior skirt are formed from different materials.

In the embodiment of FIG. 4, exterior and interior skirts 434, 406, respectively, are formed from the same material. Exterior and interior skirts 434, 406, respectively, may be a natural or biological material such as pericardium or another membranous tissue such as intestinal submucosa. Alternatively, exterior and interior skirts 434, 406, respectively, may be a low-porosity woven fabric, such as polyester, Dacron fabric, or PTFE, which creates a one-way fluid passage when attached to the stent. In one embodiment, exterior and interior skirts 434, 406, respectively, may be a knit or woven polyester, such as a polyester or PTFE knit, which can be utilized when it is desired to provide a medium for tissue ingrowth and the ability for the fabric to stretch to conform to a curved surface. Polyester velour fabrics may alternatively be used, such as when it is desired to provide a medium for tissue ingrowth on one side and a smooth surface on the other side. These and other appropriate cardiovascular fabrics are commercially available from Bard Peripheral Vascular, Inc. of Tempe, Ariz., for example. Elastomeric materials such as but not limited to polyurethane may also be used as a material for exterior and interior skirts 434, 406. In another embodiment hereof, as shown in FIG. 5, exterior and interior skirts 534, 506, respectively, of a transcatheter valve prosthesis 500 are formed from different materials. In the embodiment of FIG. 5, for example, exterior skirt 534 is formed from a fabric material such as those listed above and interior skirt 506 is formed from a natural or biological material such as those listed above. Different material combinations for the exterior and interior skirts may vary according to application.

Figure 6:
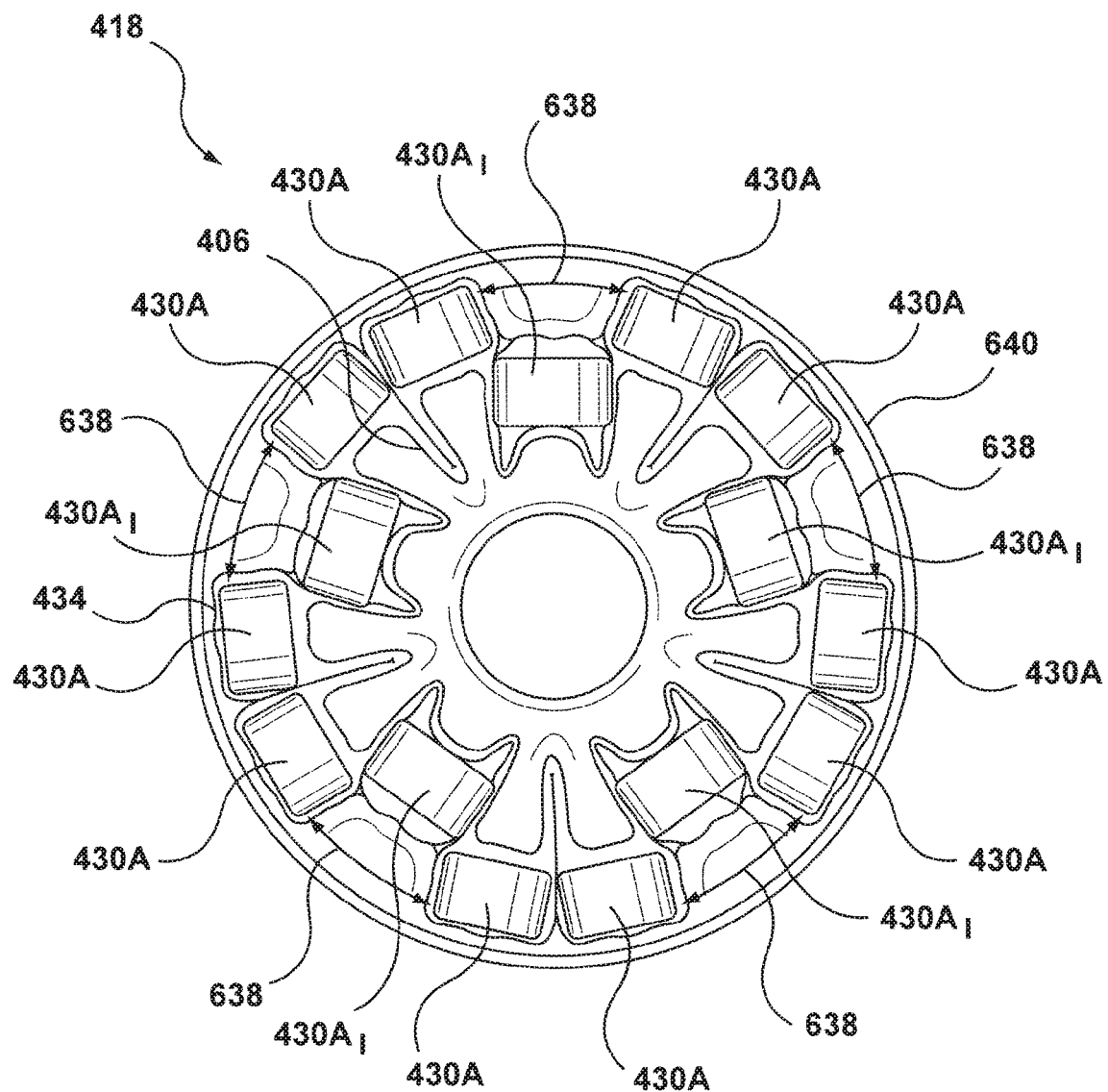
FIG. 6 is an end view of an inflow end of the transcatheter valve prosthesis of FIG. 4, wherein the transcatheter valve prosthesis is in a compressed or delivery configuration and disposed within a delivery sheath.
Figure 7:
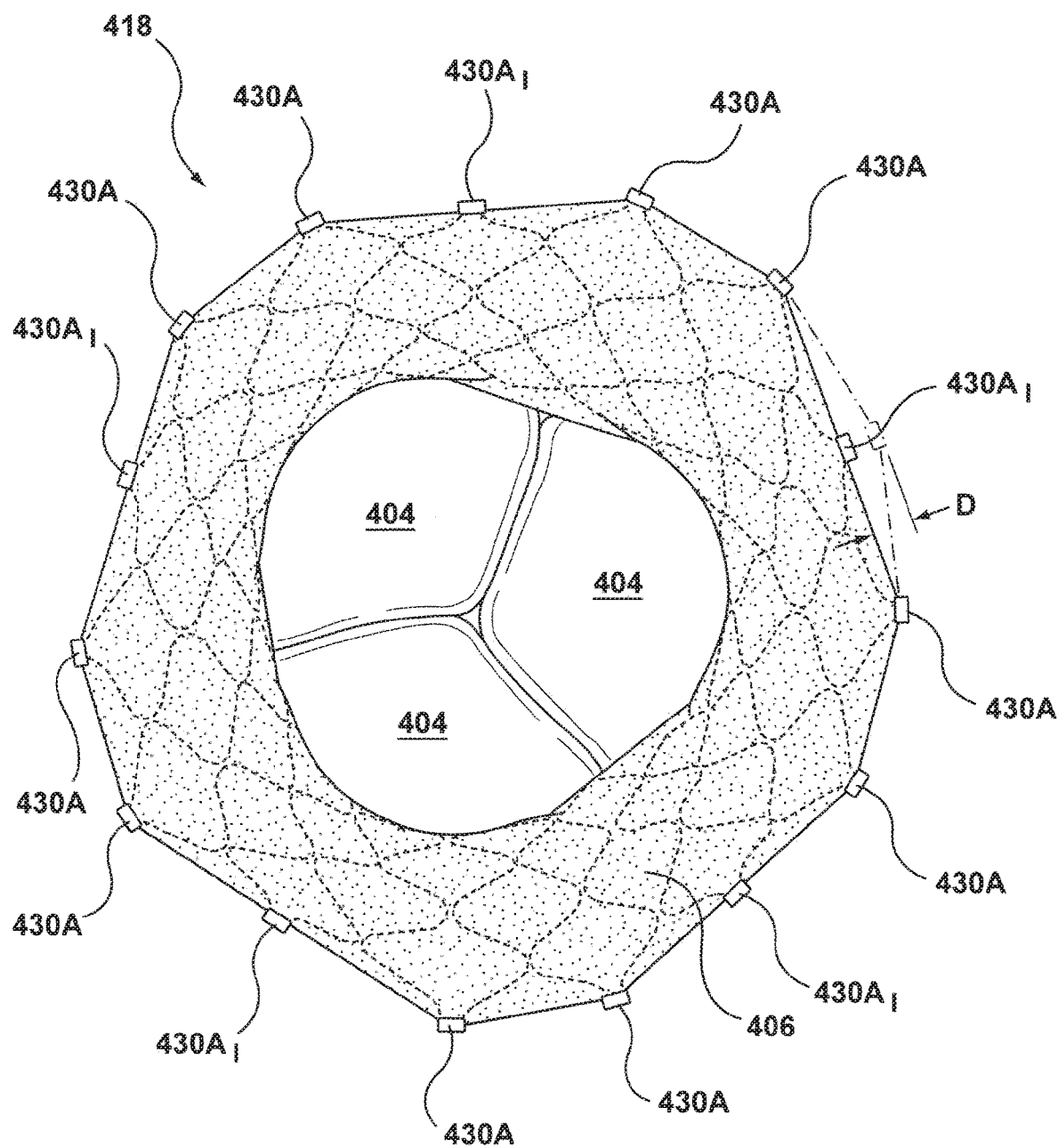
FIG. 7 is an end view of an inflow end of the transcatheter valve prosthesis of FIG. 4, wherein the transcatheter valve prosthesis is in a deployed or expanded configuration.

Stent 402 has a compressed configuration for delivery within a vasculature as shown in FIG. 6 and an expanded configuration for deployment within a native heart valve as shown in FIG. 7. FIG. 6 is an end view of inflow or distal end 418 of transcatheter valve prosthesis 400, with transcatheter valve prosthesis 400 compressed or contracted into a delivery sheath 640 of a delivery system or catheter. As previously mentioned, in order to provide a low profile yet still accommodate exterior skirt 434, at least one endmost crown 430A$_I$ of transcatheter valve prosthesis 400 is positioned radially inwards or is radially offset with respect to the remaining endmost crowns 430A formed at inflow end 418 of stent 402. For sake of clarity, endmost crowns that are positioned radially inwards are herein referred to as offset endmost crowns 430A$_I$. By relocating at least one offset endmost crown 430A$_I$ radially inward, a circumferentially-extending gap 638 (shown on FIG. 6) is formed or created between the endmost crowns 430A adjacent to the at least one offset endmost crown 430A$_I$ in order to accommodate the material of exterior skirt 434. "Circumferentially-extending gap" as used herein refers to a gap or space that extends in a circumferential direction between two endmost crowns 430 that are directly adjacent to or next to an offset endmost crown 430A$_I$.

In the embodiment of FIG. 6, every third endmost crown is positioned radially inwards with respect to the remaining endmost crowns in order to accommodate exterior skirt 434. The remaining endmost crowns 430A are compressed together in order to fit within delivery sheath 640 and the outer surface of each remaining endmost crown 430A presses against the inner surface of delivery sheath 640. Exterior skirt 434 is sandwiched between the inner surface of delivery sheath 640 and the outer surface of stent 402, while interior skirt 406 compresses or packs within the lumen of stent 402 and does not interfere with stent 402. By configuring offset endmost crowns 430A$_I$ to be positioned radially inward, the delivery configuration of transcatheter valve prosthesis 400 is predictable and organized, thereby leading to relatively lower and predictable loading forces, deployment forces, and/or recapture forces. The number of offset endmost crowns may vary according to application. Although FIG. 6 illustrates every third endmost crown being positioned radially inwards with respect to the remaining endmost crowns, only one endmost crown is required to be positioned radially inwards in order to accommodate exterior skirt 434. Other embodiments hereof may include every fourth endmost crown being positioned radially inwards with respect to the remaining endmost crowns or may include every other endmost crown being positioned radially inwards with respect to the remaining endmost crowns. Although deemed most beneficial in a transcatheter valve prosthesis such as transcatheter valve prosthesis 400 having a double layer of skirt material extending over at least a portion of the endmost side openings of the stent, positioning one or more endmost crowns radially inwards with respect to the remaining endmost crowns may be utilized on any transcatheter prostheses having an exterior skirt in order to accommodate the exterior skirt material and ensure that the delivery configuration of the transcatheter valve prosthesis is predictable and organized.

In order to configure offset endmost crowns 430A$_I$ of transcatheter valve prosthesis 400 to be positioned radially inwards with respect to the remaining endmost crowns 430A formed at inflow end 418 of stent 402, stent 402 is formed in the expanded or deployed configuration shown in FIG. 7. FIG. 7 is an end view of inflow or distal end 418 of transcatheter valve prosthesis 400, and every third endmost crown is positioned radially inwards with respect to the remaining endmost crowns as shown. In this embodiment, when stent 402 is in the expanded configuration, each offset endmost crown 430A$_I$ is positioned radially inwards a predetermined distance D (shown in phantom in FIG. 7) of 1 millimeter relative to the radial position of the remaining endmost crowns 430A. In order to position an offset endmost crown 430A$_I$ radially inwards, at least endmost struts 428A that are immediately adjacent to the offset endmost crown 430A$_I$ bend radially inwards. More particularly, endmost struts 428A that meet at or are directly associated with the offset endmost crown 430A$_I$ are heat set or shape set to bend towards the center of stent 402 to position the offset endmost crown 430A$_I$ radially inwards by a predetermined distance. "Radially inwards" as used herein includes positioning a selected or particular crown a predetermined distance closer to or towards the center of the transcatheter valve prosthesis. However, as will be understood by one of ordinary skill in the art, the predetermined distance may vary according to application and thus in another embodiment hereof, the offset endmost crowns 430A$_I$ may be positioned radially inwards a predetermined distance of between 0.5 and 1.5 millimeters relative to the radial position of the remaining endmost crowns 430A. When transcatheter valve prosthesis 400 is compressed or contracted for delivery, the spacial relationship of each endmost crown relative to the center of the transcatheter valve prosthesis holds or is maintained such that transcatheter valve prosthesis 400 has the compressed or delivery configuration shown in FIG. 6 in which every third endmost crown is positioned radially inwards with respect to the remaining endmost crowns. In another embodiment hereof (not shown), struts and crowns proximal to endmost struts 428A may also be heat set or shape set to bend towards a center line or longitudinal axis of stent 402 such that the offset endmost crown 430A$_I$ is positioned radially inwards by a predetermined distance. For example, in another embodiment hereof, the struts and crowns that form a side opening adjacent to offset endmost crown 430A$_I$ may be heat set or shape set to bend towards a center line or longitudinal axis of stent 402 in order to position offset endmost crown 430A$_I$ radially inwards.

In another embodiment hereof, in addition to and/or as an alternative to positioning at least one endmost crown radially inward in order to accommodate an exterior skirt, a single layer skirt that passes through or traverses the stent may be utilized. Stated another way, in order to avoid a double layer of skirt material at the inflow end of the transcatheter valve prosthesis, another embodiment hereof is related to a single skirt component that includes an interior portion and an exterior portion. Since the first and second portions of the skirt do not overlap, only a single layer of skirt material covers either an inner surface or outer surface of the stent and thus there is sufficient room for the stent struts to be compressed together and packed into the delivery sheath without inadvertently pushing any struts/crowns radially inward.

Figure 8:
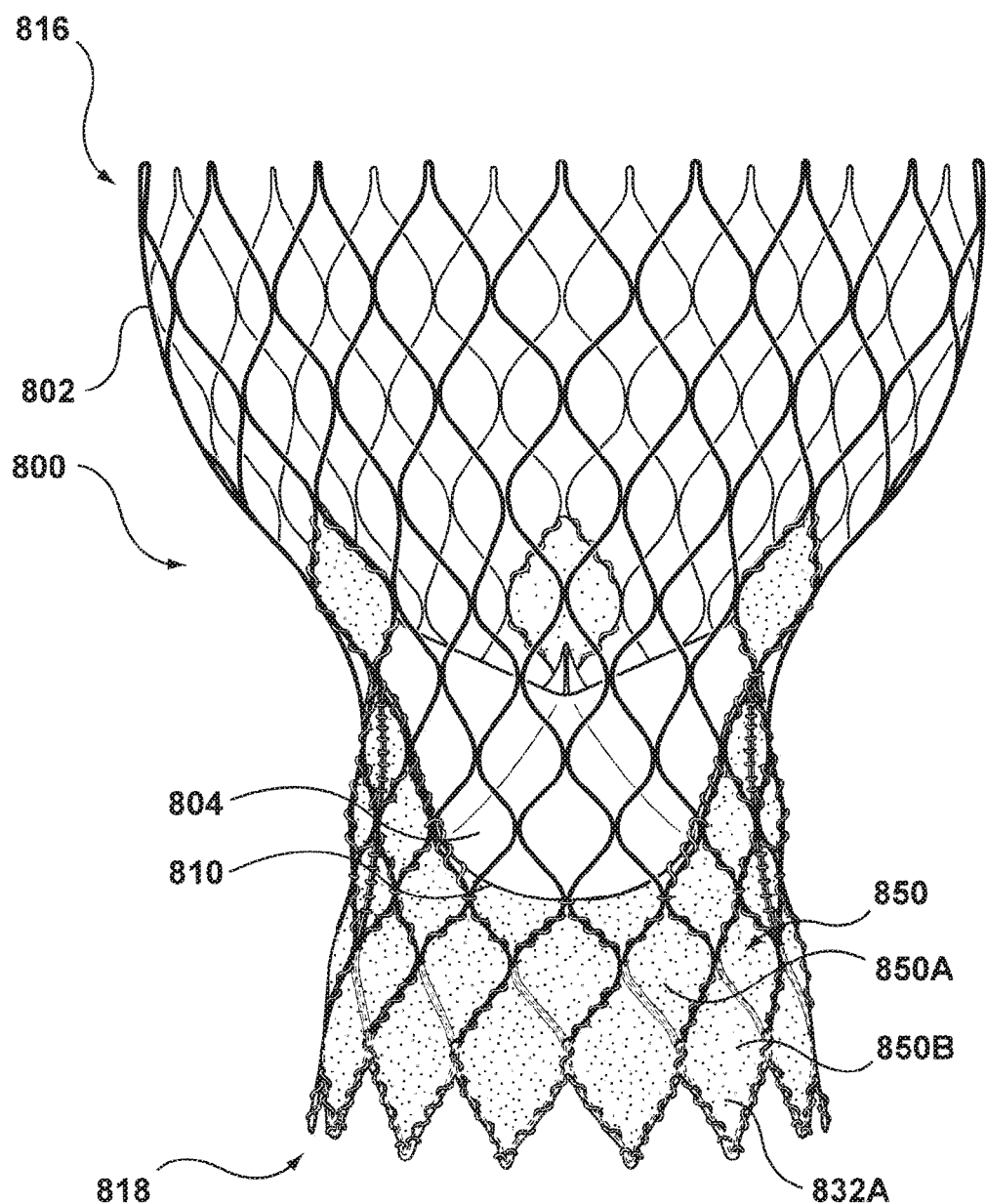
FIG. 8 is a side view illustration of a transcatheter valve prosthesis including a skirt attached to a tubular stent thereof, the transcatheter valve prosthesis being shown in a deployed or expanded configuration, wherein a first or interior portion of the skirt extends around an inner surface of the stent and a second or exterior portion of the skirt extends around an outer surface of the stent.

More particularly, with reference to FIG. 8, a side view of a transcatheter valve prosthesis 800 having a first end 816 and a second end 818 is shown. Valve prosthesis 800 is configured for replacement for an aortic valve such that second end 818 functions as an inflow or distal end thereof and extends into and anchors within the aortic annulus of a patient's left ventricle, while first end 816 functions as an outflow or proximal end of transcatheter valve prosthesis 800 and is positioned in the patient's ascending aorta. Similar to transcatheter valve prosthesis 100, transcatheter valve prosthesis 800 includes a tubular stent 802, a skirt 850, and a prosthetic valve component that includes leaflets 804 disposed within stent 802. However, while skirt 106 of transcatheter valve prosthesis 100 is solely interior and encloses or lines the inner surface of stent 102, skirt 850 of transcatheter valve prosthesis 800 is a single component that includes a first or interior portion 850A attached to and covering an inner circumferential surface of stent 802 and a second or exterior portion 850B attached to and covering an outer circumferential surface of an inflow end 818 of stent 802. As will be explained in more detail herein, interior and exterior portions 850A, 850B of skirt 850 do not overlap such that only a single layer of skirt material covers the stent at any longitudinal position thereof. Although described separately for illustrative purposes herein, it will be understood by one of ordinary skill in the art that interior and exterior portions 850A, 850B of skirt 850 are continuous, integral sections or portions of a single component, i.e., skirt 850. The interior and exterior portions of skirt 850A are non-overlapping such that no portion of stent 802 is sandwiched or positioned between layers of skirt material. In an embodiment, skirt 850 is a one-piece component and has no seams thereon or there-through prior to assembly onto stent 802. The prosthetic valve component that includes leaflets 804 is disposed within and secured to interior portion 850A of skirt 850, and exterior portion 850B of skirt 850 functions to block any retrograde flow within the native valve, thereby preventing undesired regurgitation and preventing blood stagnation in and around the native valve sinuses. In addition, when transcatheter valve prosthesis 800 is deployed, exterior portion 850B of skirt 850 is configured to substantially fill any/all gaps or cavities/crevices between the outer surface of stent 802 and native valve tissue. Exterior portion 850B of skirt 850 functions as a continuous circumferential seal around transcatheter valve prosthesis 800 to block or prevent blood flow around the outer perimeter of the prosthesis, thereby minimizing and/or eliminating any paravalvular leakage at the implantation site.

Figure 11:
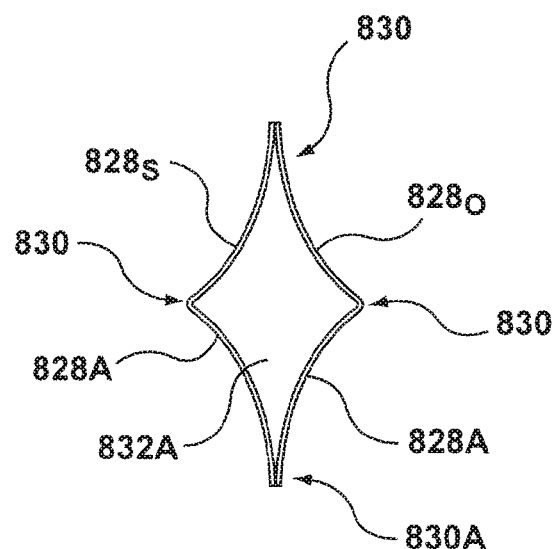
FIG. 11 is a side view of a single endmost side opening of the stent of the transcatheter valve prosthesis of FIG. 8.

Similar to previous embodiments described above, stent 802 includes a plurality of crowns 830 and a plurality of struts 828 with each crown being formed between a pair of opposing struts. The plurality of crowns 830 and the plurality of struts 828 define a plurality of side openings 832 of the tubular stent 802 as described above with respect to FIG. 4. Stent 802 has endmost side openings 832A at inflow or distal end 818 thereof. With additional reference to FIG. 11, which is a side view of a single endmost side opening 832A of stent 802, each endmost side opening 832A is formed via two pairs of opposing crowns 830, with one crown being an endmost crown 830A, and four struts therebetween. For sake of illustration, the struts immediately adjacent to endmost crown 830A are herein referred to as endmost struts 828A and the remaining two struts of each endmost side opening 832A are herein referred to as a secured strut 828$_S$ and an overpassed strut 828$_O$. As will be explained in more detail, although the struts themselves are similar structures having similar configurations, secured strut 828$_S$ and overpassed strut 828$_O$ are herein differentiated from each other due to their respective roles during attachment of exterior portion 850B of skirt 850 thereto.

Exterior portion 850B of skirt 850 longitudinally extends over or covers at least endmost side openings 832A of stent 802. In an embodiment hereof, as shown in FIG. 8, exterior portion 850B of skirt 850 longitudinally extends over or covers only endmost side openings 832A of stent 802. However, exterior portion 850B of skirt 850 may extend over a longer portion of transcatheter valve prosthesis 800 such as but not limited to two or more rows of side openings at inflow or distal end 818 thereof. Interior portion 850A of skirt 850 longitudinally extends from a proximal end or edge of exterior portion 850B of skirt 850 up to bases 810 of leaflets 806. As such, in this embodiment, only a single layer of skirt material, i.e., exterior portion 850B of skirt 850, extends over inflow or distal end 818 of stent 802. Skirt 850 may be a natural or biological material such as pericardium or another membranous tissue such as intestinal submucosa. Alternatively, skirt 850 may be a low-porosity woven fabric, such as polyester, Dacron fabric, or PTFE, which creates a one-way fluid passage when attached to the stent. In one embodiment, skirt 850 may be a knit or woven polyester, such as a polyester or PTFE knit, which can be utilized when it is desired to provide a medium for tissue ingrowth and the ability for the fabric to stretch to conform to a curved surface. Polyester velour fabrics may alternatively be used, such as when it is desired to provide a medium for tissue ingrowth on one side and a smooth surface on the other side. These and other appropriate cardiovascular fabrics are commercially available from Bard Peripheral Vascular, Inc. of Tempe, Ariz., for example. Elastomeric materials such as but not limited to polyurethane may also be used as a material for skirt 850.

Figure 9:
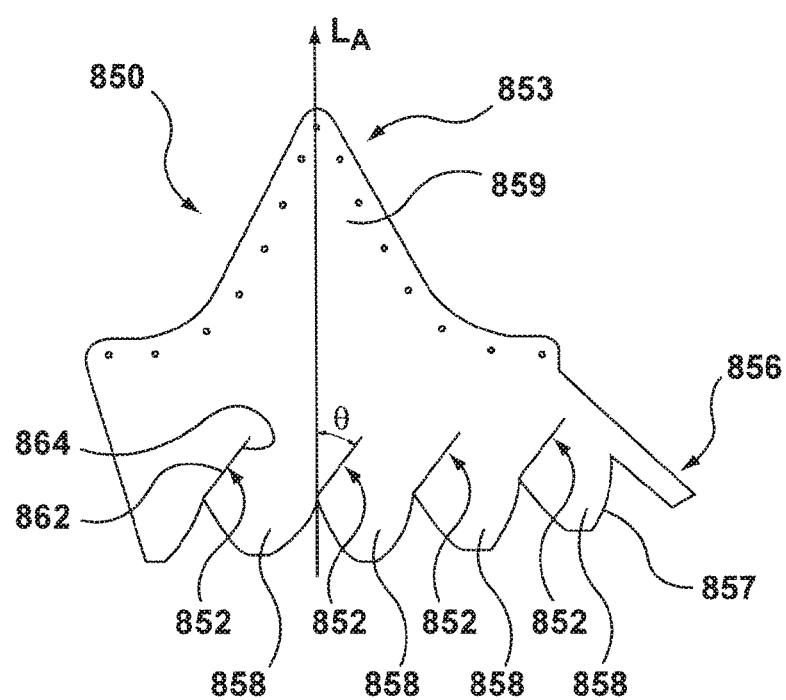
FIG. 9 illustrates a portion of the skirt of FIG. 8 removed from the transcatheter valve prosthesis and laid flat for illustrative purposes only.

In order for skirt 850 to pass through or transverse stent 802, skirt 850 includes a plurality of cuts 852 therein that are positioned to permit exterior portion 850B of skirt 850 to extend from the inner surface to the outer surface of stent 802 through, certain side openings 832 thereof. More particularly, FIG. 9 illustrates a portion of skirt 850 removed from transcatheter valve prosthesis 800 and laid flat for illustrative purposes only. Skirt 850 includes a proximal end 853 having a triangular edge 859 that corresponds to or substantially matches the shape of bases 810 of leaflets 804 and a distal end 856 having a sinusoidal or wavy edge 857 with alternating peaks and valleys that corresponds to or substantially matches the shape of inflow or distal end 818 of stent 802. In an embodiment hereof, each cut 852 stems from a valley of wavy edge 857 at an angle $\ominus$ relative to a longitudinal axis $L_A$ of transcatheter valve prosthesis 800 which may range between 0 and 60 degrees, depending upon the geometry of the struts of stent 802. Further, each cut 852 may have a length between 2 mm to 3 cm, depending upon the geometry of the struts of stent 802, and in an embodiment, the length of each cut 852 is equal to the length of secured strut $828_S$ of endmost side opening 832A. The plurality of cuts 852 create or form a plurality of individual portions or flaps 858 therebetween such that a single flap is created between two adjacent cuts, with each flap 858 longitudinally extending from the proximal ends of cuts 852 to the wavy edge 857 of skirt 850. Each cut 852 forms a first edge 862 on skirt 850 and a second or opposing edge 864 on skirt 850, with first edge 862 being disposed on material that forms interior portion 850A of skirt 850 and second edge 864 being disposed on material that forms exterior portion 850B of skirt 850 as will be explained in more detail herein with respect to FIG. 10A.

Figure 10:
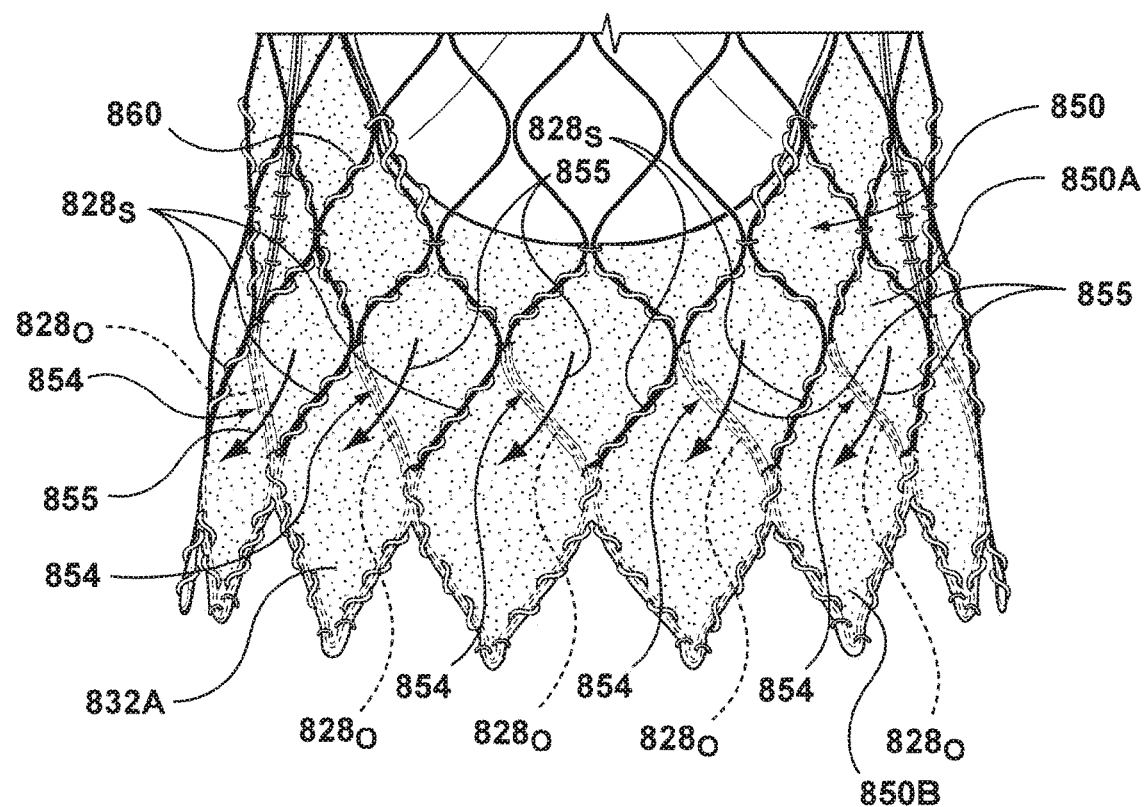
FIG. 10 is an enlarged side view illustration of an inflow end of the transcatheter valve prosthesis of FIG. 8.
Figure 10A:
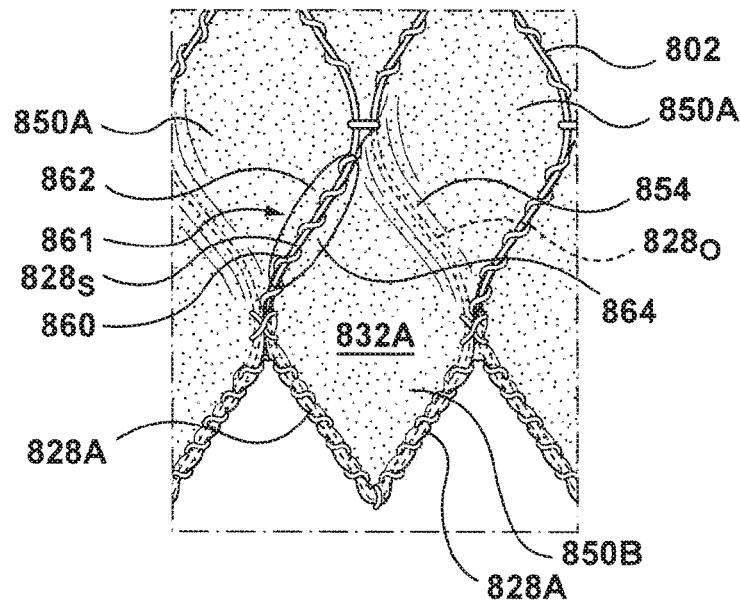
FIG. 10A is an enlarged side view illustration of a portion of an inflow end of the transcatheter valve prosthesis of FIG. 8.

With additional reference to FIG. 10 and FIG. 10A, when being placed or assembled onto stent 802, skirt 850 is positioned on the inner surface of the stent and interior portion 850A of skirt 850 is coupled thereto with a plurality of stitches 860. Interior portion 850A of skirt 850 includes proximal end 853 of skirt 850 and extends to a proximal end of the plurality of cuts 852. Exterior portion 850B is then positioned onto the outer surface of stent 802. More particularly, each flap 858 of exterior portion 850B of skirt 850 is passed or directed through a respective side opening 832 (that is adjacent to an endmost side opening 832A to be covered by the flap 858 of exterior portion 850B of skirt 850) of stent 802 and over an overpassed or covered strut $828_O$ (shown in phantom on FIG. 10) of the endmost side opening 832A as indicated by directional arrows 855 shown on FIG. 10 and herein referred to as overpass or transition zones 854 shown on FIG. 10. Once flaps 858 are on the outer surface of the stent, flaps 858 extend over endmost side openings 832A with the plurality of cuts 852 positioned adjacent to secured struts $828_S$ of endmost side openings 832A.

Flaps 858 of exterior portion 850B of skirt 850 are then secured or attached to stent 802 such that each flap 858 sealingly covers or extends over an endmost side opening 832A of stent 802. More particularly, each flap 858 is sewn to three struts, i.e., both of endmost struts 828A and secured strut $828_S$, of each endmost side opening 832A. Notably, exterior portion 850B of skirt 850 extends or passes over the fourth strut of each endmost side opening 832A, i.e., overpassed strut $828_O$, but is not attached or sewn to overpassed strut $828_O$. Stated another way, there is no seam at overpass zones 854 in which skirt 850 passes or flows from an inner surface of stent 802 to an outer surface of stent 802. Rather, at overpass zones 854 as shown on FIG. 10, the material of skirt 850 passes or extends over overpassed struts $828_O$ of endmost side openings 832A of stent 802 in order to maintain valvular sealing at overpass zones 854. The amount of material is minimized when skirt 850 passes or flows from an inner surface of stent 802 to an outer surface of stent 802.

In addition, as best shown on FIG. 10A, when flaps 858 are positioned over endmost side openings 832A, the plurality of cuts 852 are positioned adjacent to secured struts $828_S$ of endmost side opening 832 of stent 802. Interior portion 850A of skirt 850 have first edges 862 of cuts 852 and exterior portions 850B of skirt 850 have second edges 864 of cuts 852, with secured struts $828_S$ being sandwiched or positioned between edges 862, 864 of interior, exterior portions 850A, 850B, respectively, of skirt 850. Although secured struts $828_S$ are sandwiched between edges 862, 864 of interior, exterior portions 850A, 850B, respectively, of skirt 850, edges 862, 864 do not overlap or overlay. A single seam or row 861 of stitches 860 is utilized to couple or attach each secured struts $828_S$ to both edges 862, 864 of interior, exterior portions 850A, 850B, respectively, of skirt 850. Since no portions of interior and exterior portions 850A, 850B of skirt 850 overlap or overlay each other, only a single layer of skirt material extends over stent 802 in order to minimize the amount of material and profile of the transcatheter valve prosthesis. Skirt 850 advantageously provides interior portion 850A for securement of leaflets 804 as well as exterior portion 850B for improved sealing, while avoiding a double layer of skirt material in order to minimize the profile of the transcatheter valve prosthesis.

Although not required, transcatheter valve prosthesis 800 may also include one or more endmost crowns that are positioned radially inwards with respect to the remaining endmost crowns in order to accommodate the material of exterior skirt portion 850B and ensure that the delivery configuration of the transcatheter valve prosthesis is predictable and organized as described above with respect to the embodiments of FIGS. 4, 6, and 7. In addition, although embodiments depicted herein illustrate exterior skirts or exterior skirt portions on a transcatheter valve prosthesis configured for implantation within an aortic valve, it would be obvious to one of ordinary skill in the art that the exterior skirts or exterior skirt portions as described herein may be integrated onto a transcatheter valve prosthesis configured for implantation within other heart valves, such as a mitral valve or a pulmonary valve. The transcatheter valve prosthesis may be designed with a number of different configurations and sizes to meet the different requirements of the location in which it may be implanted.

While various embodiments according to the present invention have been described above, it should be understood that they have been presented by way of illustration and example only, and not limitation. It will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with the appended claims and their equivalents. It will also be understood that each feature of each embodiment discussed herein, and of each reference cited herein, can be used in combination with the features of any other embodiment. All patents and publications discussed herein are incorporated by reference herein in their entirety.

What is claimed is:
1. A transcatheter valve prosthesis comprising:
 a stent extending along a longitudinal axis between an inflow end and an outflow end, the stent having a compressed configuration for delivery within a vasculature and an expanded configuration for deployment within a native heart valve, the stent including a plurality of crowns and a plurality of struts with each crown being a curved segment extending between a pair of opposing struts, the curved segment being curved between a first end and a second end thereof, wherein the first end of the curved segment extends from a first strut of the pair of opposing struts and the second end of the curved segment extends from a second strut of the pair of opposing struts, wherein the plurality of crowns and the plurality of struts define a plurality of openings of the stent and the stent has endmost crowns and endmost openings formed at the inflow end thereof, wherein all of the endmost crowns are disposed at a substantially similar longitudinal position when the stent is in the expanded configuration and all of the endmost crowns are disposed about a circumference of the inflow end of the stent, all of the endmost crowns forming the inflow end at the substantially similar longitudinal position at a longitudinal end of the stent, an interior skirt coupled to and covering an inner circumferential surface of the stent;

a prosthetic valve component disposed within and secured to the interior skirt; and an exterior skirt coupled to and covering an outer circumferential surface of the stent, the exterior skirt longitudinally extending over at least the endmost openings of the stent, wherein when the stent is in at least the compressed configuration at least one endmost crown is configured to be positioned radially inwards with respect to the remaining endmost crowns formed at the inflow end of the stent, thereby forming a circumferentially-extending gap between the endmost crowns adjacent to the at least one endmost crown positioned radially inwards in order to accommodate the exterior skirt, and wherein a first distance separating the longitudinal axis and the at least one endmost crown positioned radially inwards is less than a second distance separating the longitudinal axis and the remaining endmost crowns.

2. The transcatheter valve prosthesis of claim 1, wherein when the stent is in the expanded configuration the at least one endmost crown is configured to be positioned radially inwards with respect to the remaining endmost crowns formed at the inflow end of the stent, and wherein a plane perpendicular to the longitudinal axis at the inflow end is adjacent to the endmost crowns.

3. The transcatheter valve prosthesis of claim 1, wherein when the stent is in the expanded configuration the at least one endmost crown is configured to be positioned radially inwards a distance of between 0.5 and 1.5 millimeters from the remaining endmost crowns formed at the inflow end of the stent.

4. The transcatheter valve prosthesis of claim 1, wherein every third endmost crown is configured to be positioned radially inwards with respect to the remaining endmost crowns formed at the inflow end of the stent.

5. The transcatheter valve prosthesis of claim 1, wherein at least the struts that form the endmost opening adjacent to the at least one endmost crown are configured to bend radially inwards in order to position the at least one endmost crown radially inwards with respect to the remaining endmost crowns formed at the inflow end of the stent such that the struts adjacent to the at least one endmost crown and the at least one endmost crown are bent radially inwards with respect to the remaining endmost crowns.

6. The transcatheter valve prosthesis of claim 5, wherein the interior skirt longitudinally extends over the endmost openings of the stent to the prosthetic valve component.

7. The transcatheter valve prosthesis of claim 6, wherein the exterior skirt longitudinally extends over only the endmost openings of the stent, and wherein the exterior skirt is disposed within the circumferentially-extending gap when the stent is in the compressed configuration.

8. The transcatheter valve prosthesis of claim 1, wherein the interior skirt and the exterior skirt are formed from the same material.

9. The transcatheter valve prosthesis of claim 1, wherein the interior skirt and the exterior skirt are formed from different materials.

10. A transcatheter valve prosthesis comprising:

a stent having a compressed configuration for delivery within a vasculature and an expanded configuration for deployment within a native heart valve, the stent including a plurality of crowns and a plurality of struts with each crown being a curved segment extending between a pair of opposing struts, the curved segment being curved between a first end and a second end thereof, wherein the first end of the curved segment extends from a first strut of the pair of opposing struts and the second end of the curved segment extends from a second strut of the pair of opposing struts, wherein the plurality of crowns and the plurality of struts define a plurality of openings of the stent and the stent has endmost crowns and endmost openings formed at an inflow end thereof, wherein all of the endmost crowns are disposed at a substantially similar longitudinal position when the stent is in the expanded configuration and all of the endmost crowns are disposed about a circumference of the inflow end of the stent;

a skirt coupled to and covering an outer circumferential surface of an inflow end of the stent, the skirt longitudinally extending over at least the endmost openings of the stent; and a prosthetic valve component disposed within and secured to the stent, wherein when the stent is in at least the compressed configuration at least one endmost crown is configured to be positioned radially inwards with respect to a first endmost crown adjacent to and on a first side of the endmost crown positioned radially inwards and a second endmost crown adjacent to and on an opposing second side of the endmost crown positioned radially inwards, and wherein the endmost crown positioned radially inwards is substantially similar in structure to the first endmost crown and the second endmost crown.

11. The transcatheter valve prosthesis of claim 10, wherein when the stent is in the expanded configuration the at least one endmost crown is configured to be positioned radially inwards with respect to the remaining endmost crowns formed at the inflow end of the stent, and wherein a linear axis intersects the first endmost crown, the second endmost crown, and the endmost crown positioned radially inwards.

12. The transcatheter valve prosthesis of claim 10, wherein every third endmost crown is configured to be positioned radially inwards with respect to the remaining endmost crowns formed at the inflow end of the stent.

13. The transcatheter valve prosthesis of claim 10, further comprising a second skirt coupled to and covering an inner circumferential surface of the stent.

14. The transcatheter valve prosthesis of claim 10, wherein the skirt is also coupled to and covers an inner circumferential surface of the stent.

15. A transcatheter valve prosthesis comprising:

a stent having a compressed configuration for delivery within a vasculature and an expanded configuration for deployment within a native heart valve, the stent including a plurality of crowns and a plurality of struts with each crown being a curved segment extending between a pair of opposing struts, the curved segment being curved between a first end and a second end thereof, wherein the first end of the curved segment extends from a first strut of the pair of opposing struts and the second end of the curved segment extends from a second strut of the pair of opposing struts, wherein the plurality of crowns and the plurality of struts define a plurality of openings of the stent and the stent has endmost crowns and endmost openings formed at an inflow end thereof, wherein all of the endmost crowns are disposed at a substantially similar longitudinal position when the stent is in the expanded configuration and all of the endmost crowns are disposed about a circumference of the inflow end of the stent; and a prosthetic valve component disposed within and secured to the stent, wherein when the stent is in at least the compressed configuration at least one endmost crown is configured to be positioned radially inwards with respect to the remaining endmost crowns formed at the inflow end of the stent, thereby forming a circumferentially-extending gap between the endmost crowns adjacent to the at least one endmost crown positioned radially inwards, the circumferentially-extending gap extending in a circumferential direction between two endmost crowns that are directly adjacent to the at least one endmost crown positioned radially inwards.

16. The transcatheter valve prosthesis of claim 15, wherein when the stent is in the expanded configuration the at least one endmost crown is configured to be positioned radially inwards with respect to the remaining endmost crowns formed at the inflow end of the stent.

17. The transcatheter valve prosthesis of claim 15, wherein every third endmost crown is configured to be positioned radially inwards with respect to the remaining endmost crowns formed at the inflow end of the stent.

18. The transcatheter valve prosthesis of claim 15, further comprising a skirt coupled to and covering at least an outer circumferential surface of an inflow end of the stent, the skirt longitudinally extending over at least the endmost openings of the stent and wherein a width of the circumferentially-extending gap is substantially equal to a width of the at least one endmost crown positioned radially inwards.

* * * * *